United States Patent
Kilian

(10) Patent No.: US 6,897,229 B2
(45) Date of Patent: *May 24, 2005

(54) SYNERGISTIC COMBINATION COMPRISING ROFLUMILAST AND A PDE-3 INHIBITOR

(75) Inventor: Ulrich Kilian, Reichenau (DE)

(73) Assignee: Altana Pharma AG, Constance (DE)

(*) Notice: Subject to any disclaimer, the term of this patent is extended or adjusted under 35 U.S.C. 154(b) by 0 days.

This patent is subject to a terminal disclaimer.

(21) Appl. No.: 10/286,915

(22) Filed: Nov. 4, 2002

(65) Prior Publication Data

US 2003/0050329 A1 Mar. 13, 2003

Related U.S. Application Data

(63) Continuation of application No. 09/959,599, filed as application No. PCT/EP00/03838 on Apr. 27, 2000, now Pat. No. 6,498,173.

(30) Foreign Application Priority Data

May 4, 1999 (EP) .............................. 99108808

(51) Int. Cl.$^7$ .................... A61K 31/44; A61K 31/4166; A61K 31/501
(52) U.S. Cl. .................. 514/352; 514/252.06; 514/334; 514/398
(58) Field of Search ............................ 514/352, 252.06, 514/334, 398

(56) References Cited

U.S. PATENT DOCUMENTS 5,223,504 A 6/1993 Noverola et al. ........... 514/263
5,712,298 A 1/1998 Amschler ................... 514/352
5,874,437 A 2/1999 Garvey et al. .............. 514/258

FOREIGN PATENT DOCUMENTS

EP 0 435 811 A1 7/1991

OTHER PUBLICATIONS

Johnson–Mills et al., *Biochemical Pharmacology*, vol. 56, pp. 1065–1073, 1998.

Germain et al., *Eur Respir J.*, : 12 (6) : pp. 1334–1339, 1998.

Banner et al., British Journal of Pharmacology, 116: pp. 3169–3175, 1995.

Killian et al; The European Respiratory Journal, vol. 9, Supplement 23, Sep. 1996, P0253 "Distinct Pharmacological Effects of PDE3, PDE4 or PDE3 + PDE4 inhibition in guinea pigs".

Underwood et al; JPET 270; pp. 250–259, 1994; "Comparison of Phosphodiesterase III, IV and dual III/IV inhibitors on bronchospasm and pulmonary eosinophil influx in guinea pigs".

Chem Abstract 128: 176402 (Apr. 13, 1998).

Hatzelmann et al., *Phosphodiesterase Inhibitors*, Academic Press, pp. 147–160, 1996.

*Primary Examiner*—Phyllis G. Spivack
(74) *Attorney, Agent, or Firm*—Nath & Associates PLLC; Joshua B. Goldberg; Sheldon M. McGee

(57) ABSTRACT

The $PDE_4$ inhibitor N-(3,5-dichloropyrid-4-yl)-3-cyclopropylmethoxy-4-difluoromethoxy benzamide, a pharmacologically tolerable salt or N-oxide thereof, in combination with a $PDE_3$ inhibitor is disclosed for use in inhibiting bronchospasms and treating acute obstructive bronchitis, asthma or COPD.

9 Claims, No Drawings

SYNERGISTIC COMBINATION COMPRISING ROFLUMILAST AND A PDE-3 INHIBITOR

This application is a continuation application of U.S. patent application Ser. No. 09/959,599, filed Dec. 13, 2001 U.S. Pat. No. 6,498,173, which was an application under 35 U.S.C. 371 of International Application No. PCT/EP00/03838, with an International Filing Date of Apr. 27, 2000, the entire contents of which are hereby incorporated by reference in its entirety.

FIELD OF APPLICATION OF THE INVENTION

The invention relates to the combination of N-(3,5-dichloropyrid-4-yl)-3-cyclopropyimethoxy-4-difluoromethoxybenzamide, its pharmacologically tolerable salts or its N-oxide with known active compounds from the class of PDE3 inhibitors for therapeutic purposes.

KNOWN TECHNICAL BACKGROUND

The substances used in the combination according to the invention are, on the one hand, N-(3,5-dichloropyrid-4-yl)-3-cyclopropylmethoxy-4-difluoromethoxybenzamide, its pharmacologically tolerable salts or its N-oxide [=N-(3,5-dichloro-1-oxypyrid-4-yl)-3-cyclopropylmethoxy-4-difluoromethoxybenzamide], all of them PDE4 inhibitors, which are described in the international application WO 95/01338 and, on the other hand, known active compounds from the class of PDE3 inhibitors.

Cyclic adenosine monophosphate (cAMP) and cyclic guanosine monophosphate (cGMP) are ubiquitous intracellular second messengers which are involved in many biological processes which are induced by a huge variety of extracellular stimulants. The inactivation (metabolization) of cAMP and cGMP is effected by enzymes of the cyclic nucleotide phosphodiesterase (PDE) type. At least nine different families of PDE isoenzymes have meanwhile been identified (PDE1 to PDE9).

The PDE3 and PDE4 isoenzyme families caused particular interest; a definitive role in the inactivation of cAMP is ascribed to both. Inhibitors of these isoenzymes exhibit actions on the airways, on the peripheral blood pressure, on the central nervous system (e.g. increase in respiratory rates) and antiinflammatory actions.

The effect on the airways is essentially ascribed to the inhibition of PDE3 and, to a minor extent, also to the inhibition of PDE4. The effects on the blood pressure is regarded as mediated by PDE3, while the anti-inflammatory action and the action on the central nervous system are assigned to the inhibition of PDE4.

The combined use of the PDE4 inhibitor N-(3,5-dichloropyrid-4-yl)-3-cyclopropylmethoxy-4-difluoromethoxybenzamide, its pharmacologically tolerable salts or its N-oxide with a PDE3 inhibitor in the sense according to the invention has still not been described in the prior art.

SUBJECT OF THE INVENTION

The invention relates to the combined use of N-(3,5-dichloropyrid-4-yl)-3-cyclopropylmethoxy-4-difluoromethoxybenzamide, its pharmacologically tolerable salts or its N-oxide with a PDE3 inhibitor in the treatment of disease conditions which are based on acute or chronic obstruction of vessels and/or bronchi and/or on acute or chronic inflammation.

The preparation of N-(3,5-dichloropyrid-4-yl)-3-cyclopropylmethoxy-4-difluoromethoxybenzamide, its pharmacologically tolerable salts and its N-oxide and the use of these compounds as phosphodiesterase (PDE) 4 inhibitors is described in the international application WO 95/01338.

Pharmacologically tolerable salts of N-(3,5-dichloropyrid-4-yl)-3-cyclopropylmethoxy-4-difluoromethoxybenzamide which may be mentioned are, for example, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

PDE3 inhibitors which can be employed according to the invention and which may be mentioned by way of example are those described or claimed in the following patents and patent applications: EP 0 653 426, EP 0 294 647, EP 0 357 788, EP 0 220 044, EP 0 326 307, EP 0 207 500, EP 0 406 958, EP 0 150 937, EP 0 075 463, EP 0 272 914, EP 0 112 987, U.S. Pat. No. 4,963,561, U.S. Pat. No. 5,141,931, WO 96/15117, DE 28 25 048, DE 27 27 481, DE 28 47 621, DE 30 44 568, DE 28 37 161 and DE 30 21 792.

The following PDE3 inhibitors are to be emphasized here: UK-1745, (-)-(R)-NSP-307, EMD-57033, WIN-62582, WIN-63291, NSP-307, NSP-306, CI-930, SKF-95654, KF-15232, MS-857, REVIZINONE, CI-LOSTAMIDE, AMIPIZONE, SIGUAZODAN, CARBAZERAN, BEMORADAN and MOTAPIZONE. MILRINONE, ENOXIMONE and PIMOBENDAN are particularly to be emphasized.

As a result of simultaneous inhibition of the two underlying metabolization routes (PDE3 and PDE4), a relative increase in the intracellular concentration of cyclic adenosine monophosphate can occur.

The biological effects of the combination following therefrom are not inevitably additive or even super-additive on cellular model systems. Surprisingly, in anesthetized, spontaneously breathing guinea-pigs treated with histamine, after administration of the combination of N-(3,5-dichloropyrid-4-yl)-3-cyclopropylmethoxy-4-difluoromethoxybenzamide with a PDE3 inhibitor a superadditive synergistic effect was observed in the inhibition of bronchospasms, while the measurements for the blood pressure and the respiratory rate remained unchanged in comparison with the individual administration of N-(3,5-dichloropyrid-4-yl)-3-cyclopropylmethoxy-4-difluoromethoxybenzamide or of a PDE3 inhibitor.

The unexpected, superadditive increase in the bronchospasmolytic activity on the combined administration of the PDE4 inhibitor N-(3,5-dichloropyrid-4-yl)-3-cyclopropylmethoxy-4-difluoromethoxybenzamide and of a PDE3 inhibitor without an influence thereby being exerted on the blood pressure or the respiratory rate, shows a particular suitability of this combination for the treatment of disease conditions such as, for example, acute, obstructive bronchitis, extrinsic or intrinsic bronchial asthma or COPD.

As a result of the combination according to the invention of N-(3,5-dichloropyrid-4-yl)-3-cyclopropylmethoxy-4-difluoromethoxybenzamide, its pharmacologically tolerable salts or its N-oxide with a PDE3 inhibitor, the individual components can be used in concentrations which on their own are not sufficiently active or not active at all. By means of this, side-effects of the individual components which would occur in the intrinsically active concentrations of N-(3,5-dichloropyrid-4-yl)-3-cyclopropylmethoxy-4-difluoromethoxybenzamide, its pharmacologically tolerable salts, its N-oxide or the PDE3 inhibitor on sole administration, are avoided by the lower concentration in the combination.

"Combined use" within the meaning of the present invention is to be understood as meaning that the individual components can be administered simultaneously in a manner which is known and customary per se [in the form of a combination medicament (as fixed or free combination)], more or less simultaneously (from one or separate pack units) or successively (directly one after the other or else also with a relatively great time interval).

In the case of more or less simultaneous administration of the individual components from separate pack units and in the case of the administration of the individual components which takes place successively, if desired a different administration form can be chosen. For example, one component can be administered by inhalation, while the other component is administered by infusion or orally.

The dose of the active compounds is of an order of magnitude customary for the dose of the individual components, it being possible, on account of the mutually positively influencing and increasing individual actions, to lower the respective doses compared with the norm on the combined administration of the active compounds. Exemplary doses for the PDE4 inhibitor N-(3,5-dichloropyrid-4-yl)-3-cyclopropylmethoxy-4-difluoromethoxybenzamide and N-(3,5-dichloro-1-oxypyrid-4-yl)-3-cyclopropylmethoxy-4-difluoromethoxybenzamide which can be mentioned are, in the case of oral administration, a daily dose of 2 µg/kg to approximately 20 µg/kg, if appropriate in the form of a number, preferably 1 to 3, individual doses.

In the case of parenteral treatment, similar or (in particular in the case of intravenous administration of the active compound), as a rule, lower doses can be used.

The dose in the case of PDE3 inhibitors is typically in a range from 0.1 to 25 mg/kg per day.

It is known to the person skilled in the art that the optimal dose of an active compound or of an active compound combination can vary as a function of the body weight, the age and the general state of the patient, and his response behavior to the active compound or the active compound combination.

Any person skilled in the art can easily fix the optimal dose and manner of administration of the active compounds necessary in each case on the basis of his/her expert knowledge.

As medicaments, the compounds according to the invention (=active compounds) are either employed as such, or preferably are mixed with suitable pharmaceutical auxiliaries or carriers, e. g. in the form of tablets, coated tablets, capsules, emulsions, suspensions or solutions, whereby the active compounds content is advantageously between 0.1 and 95% and whereby through appropriate choice of the employed pharmaceutical auxiliaries and carriers a galenic formulation can be achieved, which is exactly adapted to the active compounds and/or the desired time of effectiveness.

The person skilled in the art is familiar with auxiliaries which are suitable for the desired pharmaceutical formulations on account of his expert knowledge. In addition to solvents, gel formers, tablet auxiliaries and other active compound excipients, for example antioxidants, dispersants, emulsifiers, preservatives, solubilizers or permeation promoters, can be used.

What is claimed is:

1. A commercial pharmaceutical product, consisting of a secondary pack that contains a primary pack containing the medicament and, optionally a pack insert, the medicament containing as active compound N-(3,5-dichloropyrid-4-yl)-3-cyclopropylmethoxy-4-difluorornethoxybenzamide, a pharmacologically tolerable salt or the N-oxide thereof, wherein in that on the secondary pack, and/or on the pack insert, is indicated that N-(3,5-dichloropyrid-4-yl)-3-cyclopropylmethoxy-4-ditluoromethoxybenzamide, a pharmacologically tolerable salt or the N-oxide thereof, is used in combination with a PDE3 inhibitor in the therapeutic treatment of disease conditions which are based on acute or chronic obstruction of vessels and/or bronchi and/or on acute or chronic inflammation.

2. A method of inhibiting bronchospasms in a patient comprising administering to said patient a combination of
   a) N-(3, 5-dichloropyrid-4-yl)-3-cyclopropylmethoxy-4-difluoromethoxybenzamide or a pharmacologically tolerable salt or N-oxide thereof; and
   b) a PDE3 inhibitor,
wherein said combination achieves a synergistic effect in the inhibition of bronchospasms.

3. The method of claim 2, wherein said combination is a fixed combination for simultaneous administration.

4. The method of claim 2, wherein the compounds a) N-(3,5-dichloropyrid-4-yl)-3-cyclopropylmethoxy-4-difluoromethoxybenzamide or a pharmacologically tolerable salt or N-oxide thereof; and b) a PDE3 inhibitor are separated from each other and packaged in one unit for simultaneous or successive administration.

5. The method of claim 2, wherein the PDE3 inhibitor is selected from the group consisting of ENOXIMONE, MILRINONE, MILRINONE lactate, and PIMOBENDAN.

6. A method of treating acute, obstructive bronchitis, extrinsic or intrinsic bronchial asthma, or COPD in a patient comprising administering to said patient a pharmaceutically effective amount of a pharmaceutical composition comprising N-(3,5-dichloropyrid-4-yl)-3-cyclopropylmethoxy-4-difluoromethoxybenzamide or a pharmacologically tolerable salt or N-oxide thereof in combination with a PDE3 inhibitor.

7. The method of claim 6, wherein said combination is a fixed combination for simultaneous administration.

8. The method of claim 6, wherein the compound N-(3, 5-dichloropyrid-4-yl)-3-cyclopropylmethoxy-4-difluoromethoxybenzamide or a pharmacologically tolerable salt or N-oxide thereof and the FDE3 inhibitor are separated from each other and packaged in one unit for simultaneous or successive administration.

9. The method of claim 6, wherein the PDE3 inhibitor is selected from the group consisting of ENOXIMONE, MILRINONE, MILRINONE lactate, and PIMOBENDAN.

* * * * *

UNITED STATES PATENT AND TRADEMARK OFFICE
CERTIFICATE OF CORRECTION

PATENT NO. : 6,897,229 B2
DATED : May 24, 2005
INVENTOR(S) : Kilian

It is certified that error appears in the above-identified patent and that said Letters Patent is hereby corrected as shown below:

Column 4,
Line 15, please delete "difluorornethoxybenzamide" and replace with
-- difluoromethoxybenzamide --
Line 17, please delete "in that"
Line 19, please delete "ditluoromethoxybenzamide" and replace with
-- difluoromethoxybenzamide --
Line 27, please delete "N-(3, 5-dichloropyrid-4-yl)" and replace with
-- N-(3,5-dichloropyrid-4-yl) --
Line 57, please delete "FDE3" and replace with -- PDE3 --

Signed and Sealed this

Second Day of August, 2005

JON W. DUDAS
*Director of the United States Patent and Trademark Office*